US009285380B2

(12) United States Patent
Kasai et al.

(10) Patent No.: US 9,285,380 B2
(45) Date of Patent: Mar. 15, 2016

(54) MEASUREMENT SYSTEM, MEASUREMENT METHOD, PROGRAM FOR IMPLEMENTING THE METHOD, AND RECORDING MEDIUM FOR THE PROGRAM

(75) Inventors: Tokuo Kasai, Kyoto (JP); Takashi Nakagawa, Kyoto (JP); Minoru Kotaki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 754 days.

(21) Appl. No.: 13/509,734

(22) PCT Filed: Nov. 22, 2010

(86) PCT No.: PCT/JP2010/070846
§ 371 (c)(1),
(2), (4) Date: May 14, 2012

(87) PCT Pub. No.: WO2012/070111
PCT Pub. Date: May 31, 2012

(65) Prior Publication Data
US 2012/0288851 A1    Nov. 15, 2012

(51) Int. Cl.
*G01N 33/00*    (2006.01)
*G01N 35/00*    (2006.01)
(52) U.S. Cl.
CPC ............ *G01N 35/00732* (2013.01); *G01N 2035/00673* (2013.01)
(58) Field of Classification Search
CPC ............ G01N 35/00732; G01N 2035/00673
See application file for complete search history.

(56) References Cited

U.S. PATENT DOCUMENTS

2011/0158851 A1*  6/2011  Kitagawa .................. 422/67

FOREIGN PATENT DOCUMENTS

| JP | 01-114747 A | 5/1989 |
| JP | 05-232108 A | 9/1993 |
| JP | 07-046107 B | 5/1995 |
| JP | 09-005332 A | 1/1997 |
| JP | 11-237387 A | 8/1999 |
| JP | 2002-350434 A | 12/2002 |

(Continued)

OTHER PUBLICATIONS

International Preliminary Report on Patentability issued in corresponding International Application No. PCT/JP2010/070846 dated May 30, 2013.

(Continued)

*Primary Examiner* — Sam P Siefke
(74) *Attorney, Agent, or Firm* — Morgan, Lewis & Bockius LLP

(57) ABSTRACT

The invention relates to a measurement system MS1 provided with a plurality of loading units 10 into which a measurement tool 4 supporting a reagent is loaded. The measurement system MS1 includes reading means 2 for reading information on an analyte provider that includes identification information, and guidance means 11 for guiding the measurement tool 4 to which an analyte derived from the analyte provider has been or is to be applied, to a loading unit that is selected from the plurality of loading units 10 and individually associated with the analyte provider based on the identification information that has been read by the reading means 2. With such configuration, the measurement results obtained from the analyte derived from the analyte provider can be easily associated with the information on the analyte provider that includes the identification information.

9 Claims, 9 Drawing Sheets

(56) References Cited

FOREIGN PATENT DOCUMENTS

| JP | 2002-372547 A | 12/2002 |
| JP | 2006-030035 A | 2/2006 |
| JP | 2006-308432 A | 11/2006 |
| JP | 2009-133813 A | 6/2009 |
| WO | 88-08534 A1 | 3/1988 |

OTHER PUBLICATIONS

International Search Report issued in corresponding International Application No. PCT/JP2010/070846 dated Dec. 28, 2010.

* cited by examiner

MEASUREMENT SYSTEM, MEASUREMENT METHOD, PROGRAM FOR IMPLEMENTING THE METHOD, AND RECORDING MEDIUM FOR THE PROGRAM

The present application is a U.S. National Phase Application of International Application No. PCT/JP2010/070846, filed Nov. 22, 2010 which is incorporated herein by reference in its entirety.

TECHNICAL FIELD

The present invention relates to a measurement system which uses a measurement tool such as a biosensor, a urine test paper, or an immunochromatographic test piece to react an analyte that is a measurement object with a reagent, and read an electric current value, a difference in electric potential, or changes in color tone appearing inside or on the surface of the test piece to thereby measure body fluid components of humans or animals, and also relates to a measurement method, a program for implementing the method, and a recording medium for the program.

BACKGROUND ART

Methods for measuring body fluid components of humans or animals are described in detail in Patent Documents 1 to 3. Patent Document 1 describes a test piece in which one or a plurality of reagent layers impregnated with a chemical reaction agent is attached with equal spacing to a strip plastic support body. Patent Document 2 describes an immunochromatographic test piece and a measurement method using same. A test piece in which gold colloid particles, blue latex particles, or red latex particles are used as a label carrier is typically used as the immunochromatographic test piece. Patent Document 3 describes a test piece having an electrode and an oxidation-reduction enzyme on a support body. This test piece is used for measuring electrochemical changes (oxidation current value) during enzyme reactions. These test pieces make it possible to measure body fluid components of humans or animals in a simple manner.

However, in the measurements performed with the above-described measurement tools, a time interval of 1 min to 15 min is required till a reaction such as chemical reaction or electrochemical reaction becomes stable after the analyte derived from a human or an animal is dropped on the measurement tool. This is because a certain time is required for filtration of solid matter such as blood cells contained in the analyte and for hydration and reaction of immune substances such antibodies or reagents stored in a dry state in the test piece. In an immunochromatographic test piece, in particular, time is necessary to move the analyte on the support body.

Most small systems in which coloration or difference in electric potential of the measurement tool is read include only one location for setting the measurement tool. In addition, because a certain reaction time should be ensured, as mentioned hereinabove, in order to obtain accurate measurement result, a plurality of analytes is difficult to measure at the same time. A system that resolves this problem is described in Patent Document 4. The system described in Patent Document 4 includes a plurality of loading units for measurement tools. The measurements are conducted separately and automatically and the results are displayed for each loading unit till a reaction time corresponding to the reagent type elapses since the measurement tool has been loaded. As a result, a plurality of analytes can be measured simultaneously and randomly.

Patent Document 1: Japanese Patent Application Publication No. H5-232108
Patent Document 2: Japanese Examined Patent Publication No. H7-46107
Patent Document 3: Japanese Patent Application Publication No. H1-114747
Patent Document 4: Japanese Patent Application Publication No. 2009-133813

However, in the above-described measurement system in which the measurements can be performed simultaneously and randomly on a plurality of analytes, the user should perform an operation of verifying information on the analyte providers and an operation of confirming that the measurement tool to which the analyte derived from the analyte provider has been applied has been loaded into one of the plurality of loading units and also should associate the obtained measurement results with the information on the analyte provider. These operations are troublesome for the user.

DISCLOSURE OF THE INVENTION

The present invention has been created with the foregoing in view and it is an object of the present invention to provide a measurement system in which a plurality of analytes can be measured simultaneously and randomly, but the obtained measurement results still can be easily associated with information on the analyte provider, and also to provide a measurement method, a program for implementing the method, and a recording medium for the program.

In order to attain the aforementioned object, the present invention employs the following technical means.

The first aspect of the present invention resides in a measurement system provided with a plurality of loading units into which a measurement tool supporting a reagent is loaded, the measurement system including: reading means for reading information on an analyte provider that includes identification information; and guidance means for guiding the measurement tool to which an analyte derived from the analyte provider has been or is to be applied, to a loading unit that is selected from the plurality of loading units and individually associated with the analyte provider based on the identification information that has been read by the reading means.

It is preferred that the guidance means be formed of a plurality of display lamps disposed to correspond to the plurality of loading units, and the display lamps perform guidance by being turned on or turned off, or by changing color.

It is preferred that the guidance means be prevention means for preventing the measurement tool from being loaded into a loading unit other that the loading unit that has been individually associated with the analyte provider.

It is preferred that each of the plurality of loading units be provided with an opening for loading the measurement tool, and the prevention means close the opening of the other loading unit.

It is preferred that the guidance means be a display device displaying position information of the loading unit that has been individually associated with the analyte provider.

It is preferred that the display device be at least any one from among a display, a printer, and a voice guidance device.

It is preferred that the information on the analyte provider be recorded as a barcode, and the reading means be at least either of a barcode reader and an image recognition camera.

It is preferred that the reading means include a touch panel, the information on the analyte provider be listed and displayed in advance on the touch panel, and a user select, by touching, specific information from the information that has been listed and displayed on the touch panel.

It is preferred that each of the plurality of loading units have, in the back thereof, a sensor capable of recognizing that the measurement tool has been loaded.

It is preferred that the measurement system further include warning means for warning that the measurement tool has been erroneously loaded, when the sensor detects that the measurement tool having applied thereto the analyte derived from the analyte provider specified by the information read by the reading means, has been loaded to a loading unit other than the loading unit individually associated with the analyte provider.

The second aspect of the present invention resides in a measurement method using a measurement system provided with a plurality of loading units into which a measurement tool supporting a reagent is loaded, the measurement method including the steps of: reading information on an analyte provider that includes identification information with reading means; selecting, from the plurality of loading units, a loading unit for loading the measurement tool to which an analyte derived from the analyte provider has been or is to be applied, and individually associating the selected loading unit with the analyte provider based on the identification information; guiding, with guidance means, the measurement tool to which the analyte derived from the analyte provider has been or is to be applied, to the loading unit that has been individually associated with the analyte provider; detecting with detection means that the measurement tool has been loaded to the loading unit; and starting measurements of the measurement tool with measurement means upon detection by the detection means in the detection step that the measurement tool has been loaded into the loading unit.

It is preferred that the measurement system further include the steps of: calculating measurement results on the basis of data obtained by the measurements; and outputting, with an output device, the measurement results obtained in the step of calculating the measurement results together with the information that has been read in the step of reading the information on the analyte provider.

The third aspect of the present invention resides in a program for execution, on a computer, of operation control of a measurement system provided with a plurality of loading units into which a measurement tool supporting a reagent is loaded, the program causing the computer to execute the steps of: reading information on an analyte provider that includes identification information with reading means; selecting, from the plurality of loading units, a loading unit for loading the measurement tool to which an analyte derived from the analyte provider has been or is to be applied, and individually associating the selected loading unit with the analyte provider based on the identification information; guiding, with guidance means, the measurement tool to which the analyte derived from the analyte provider has been or is to be applied, to the loading unit that has been individually associated with the analyte provider; detecting with detection means that the measurement tool has been loaded to the loading unit; and starting measurements of the measurement tool with measurement means upon detection by the detection means in the detection step that the measurement tool has been loaded into the loading unit.

It is preferred that the program further cause the computer to execute the steps of: calculating measurement results on the basis of data obtained by the measurements; and outputting, with an output device, the measurement results obtained in the step of calculating the measurement results together with the information that has been read in the step of reading the information on the analyte provider.

It is preferred that the program further cause the computer to execute the steps of: detecting with the detection means that the measurement tool has been removed from the loading unit; and setting the loading unit to a state in which a new measurement tool can be loaded thereinto upon removal of the measurement tool from the loading unit.

The fourth aspect of the present invention resides in a computer-readable recording medium having recorded thereon the program of execution on a computer according to the third aspect of the present invention.

Other features and advantages of the present invention will become apparent from the description of embodiments of the invention which follows below with reference to the appended drawings.

BEST MODE FOR CARRYING OUT THE INVENTION

The preferred embodiments of the present invention will be described below in detail with reference to the appended drawings.

[Measurement System]

Figure 1:
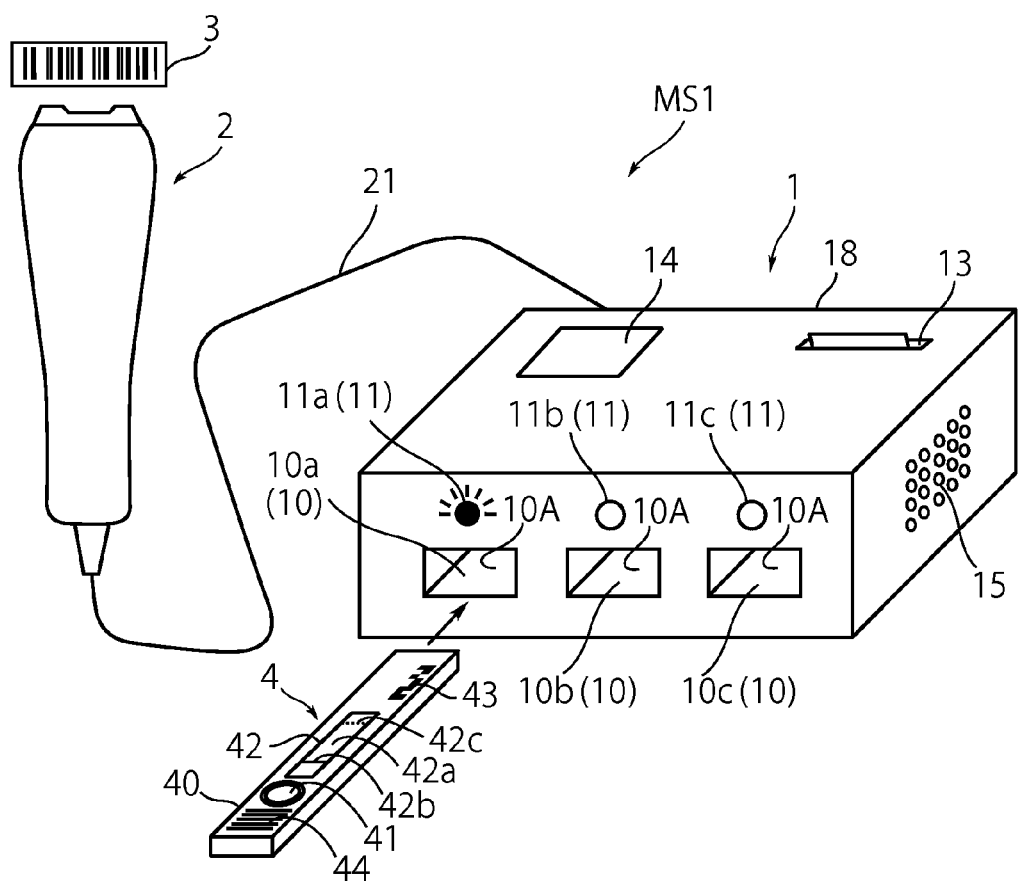
FIG. 1 is a perspective view illustrating an example of the entire measurement system in accordance with the present invention.

An example of the measurement system using the present invention will be explained below with reference to FIGS. 1 and 2. A measurement system MS1 shown in FIG. 1 uses an immunochromatographic test piece 4 as a measurement tool and is installed in a hospital or the like. The measurement system MS1 is capable of performing simultaneous and random measurements of analytes derived from a plurality of patients. The measurement system MS1 is constituted by a measurement device 1 and a barcode reader 2. The measurement device 1 and the barcode reader 2 are connected by a cable 21. The cable 21 shown in the figure is a wire cable, but it goes without saying that wireless connection may be also used. The barcode reader 2 corresponds to an example of the reading means according to the present invention. An image recognition camera can be also used as the reading means. The barcode reader 2 serves to read a barcode 3 on which information on a patient, such as identification information (ID), is recorded and which is attached to the patient chart or analyte sampling container. The patient information may include information such as the disease name or the name of the administered medicine in addition to the identification information such as an ID number or a name. The patient corresponds to an example of the analyte provider according to the present invention. Further, in the present invention, "information on the analyte provider including identification information" can include not only both the identification information and information other than the identification information, but also only the identification information.

As mentioned hereinabove, the measurement system MS1 uses the immunochromatographic test piece 4 as a measurement tool. The immunochromatographic test piece 4 serves, for example, for performing influenza testing. The immunochromatographic test piece 4 has a case 40; a support body 42a that holds a reagent is accommodated inside the case. The case 40 has a handle 44, an analyte dropping window 41, a measurement window 42, and an item identification barcode 43. The user holds the handle 44 and loads the immunochromatographic test piece 4 into a loading unit 10 by following the indications of the guidance means of the measurement system MS1. By reading the item identification barcode 43, the measurement system MS1 recognizes the measurement item of the immunochromatographic test piece 4. The user samples the liquid on a mucous membrane of the patient's pharynx or nasal cavity, and drops the analyte diluted with a diluting solution on the analyte dropping window 41. The analyte may be also dropped before the immunochromatographic test piece 4 is loaded into the loading unit 10, or may be dropped thereafter. The analyte that has been dropped moves on the support body due to the chromatographic effect. An anti-influenza virus antibody colored with gold colloid, red latex particles, or blue latex particles is included in a line 42b on the support body 42a. Where an influenza virus is present in the analyte, the influenza virus contained in the analyte is bonded to the antibody, moved due to the chromatographic effect, and trapped by the anti-influenza virus antibody immobilized on the line 42c. As a result, the coloration, which is the measurement object, is developed on the line 42c. The method for applying the analyte to the measurement tool is not limited to dropping, and can be coating, suction, or immersion, depending to the type of the measurement tool.

The measurement device 1 includes a main body case 18. The main body case 18 has a rectangular shape and is molded, for example, from a resin or a metal. The main body case accommodates a plurality of loading units 10 which are the other constituent elements of the measurement system. Openings for inserting test pieces into the loading units 10 are formed in the front surface of the main body case 18.

The measurement device 1 is provided with a plurality of loading units 10 and a corresponding number of display lamps 11. In the present embodiment, the measurement device 1 is provided with three-channel loading units 10a, 10b, 10c. The loading units 10 serve for loading the immunochromatographic test piece 4 and performing measurements. Each loading unit 10a, 10b, 10c is provided with an opening 10A for loading the immunochromatographic test piece 4. The openings 10A are disposed to match the positions of the abovementioned openings formed in the front surface of the main body case 18. The loading units 10a, 10b, 10c are suitable for performing independent measurements, and three immunochromatographic test pieces 4 can be loaded at random timings to start the measurements and obtain measurement results. For example, even when the measurements are performed in the loading unit 10a, where the remaining loading units 10b, 10c are empty, the immunochromatographic test pieces 4 can be guided to be loaded therein and the measurements of the immunochromatographic test pieces can be started. In accordance with the present invention, the term "loading" means inserting or placing a measurement tool into the loading unit 10 to enable measurements of components in the analyte applied to the measurement tool.

The display lamps 11a, 11b, 11c are disposed to correspond to the loading units 10a, 10b, 10c, respectively. The display lamp 11 is constituted, for example, by a LED lamp. The display lamp 11 corresponds to an example of the guidance means in accordance with the present invention. The display lamp 11 serves to guide the user to load the immunochromatographic test piece 4 to the loading unit 10 selected to correspond to the patent's identification information that has been read by the barcode reader 2. As a result, the patient's identification information and the immunochromatographic test piece 4 having the patient-derived analyte dropped thereonto are associated with each other. The display lamp 11 guides the user by being turned on or turned of, or by changing the color. The display lamp being "turned on" means not only that two of the three display lamps 11 are turned off and one is turned on, but also that two of the three display lamps are usually turned on and one display lamp is turned off, thereby guiding the user to the loading unit 10 corresponding to the display lamp 11 that has been turned off. Further, not only the continuously turned-on or turned-off state of a random display lamp 11, but also a flickering state is included. The number of the loading units 10 and display lamps 11 is not limited to three and can be selected from 2 to 10.

A display 14 and a printer 13 are disposed on the upper surface of the main body case 18 of the measurement device 1. The display 14 serves to display the association of patient's information, measurement items, and measurement results corresponding to the loading units 10a, 10b, 10c. For example, a liquid crystal display (LCD) is used as the display 14. The printer 13 serves to output the associated patient's information and measurement results. The printer 13 and the display 14 are display devices and also function as warning means. A speaker 15 is disposed on the side surface of the main body case 18 of the measurement device 1. The speaker 15 is used to generate a warning sound when the user mistakenly selects the loading position of the immunochromatographic test piece 4 or forgets to remove the immunochromatographic test piece 4 after the measurements thereof have been completed. The speaker 15 corresponds to an example of voice guidance device in accordance with the present invention.

Figure 2:
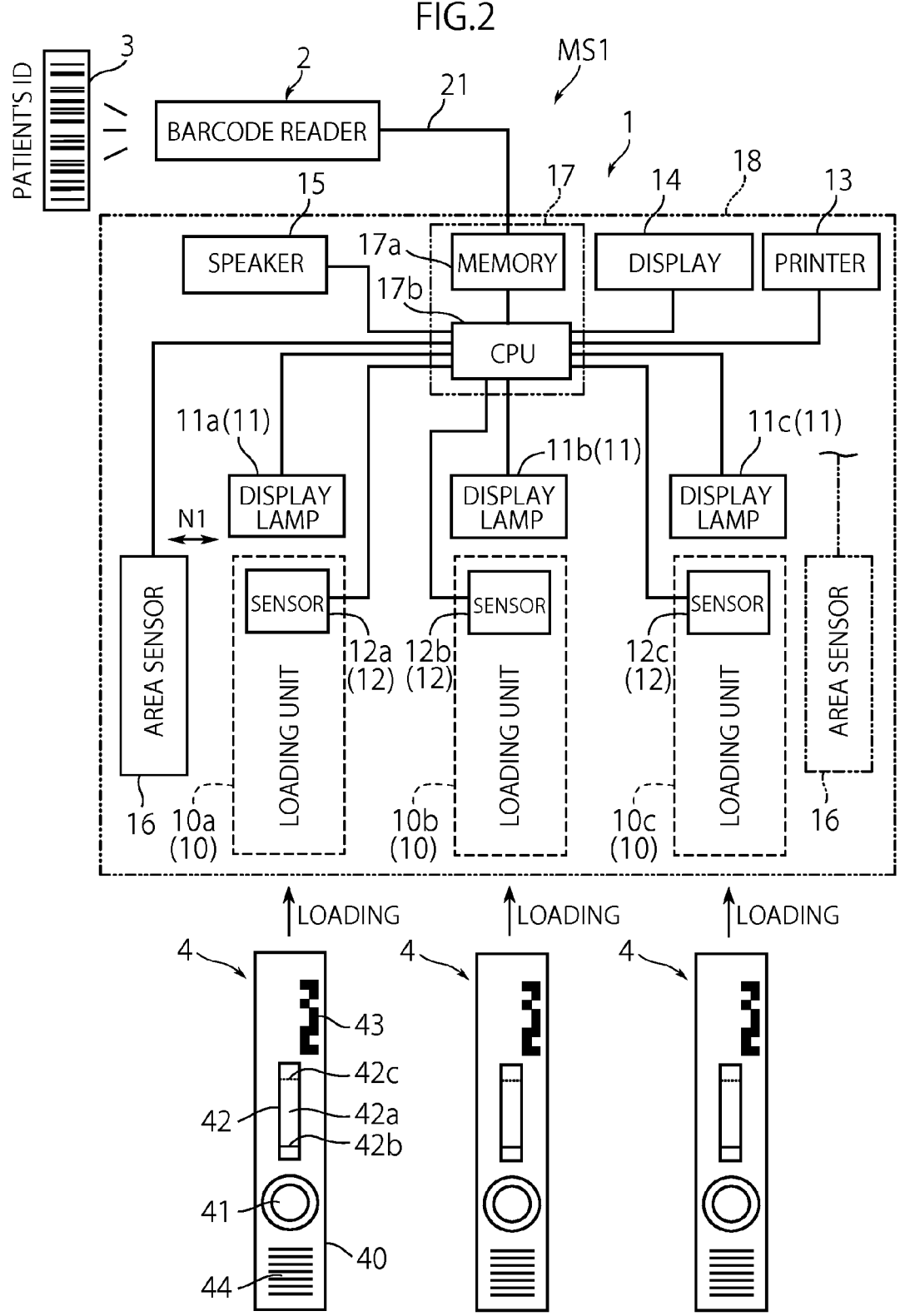
FIG. 2 is a block diagram illustrating the relationship between constituent elements in the measurement system shown in FIG. 1.

As shown in FIG. 2, the measurement device 1 includes a control unit 17 and an area sensor 16 in addition to the above-described loading unit 10, display lamps 11, display 14, printer 13, and speaker 15. A sensor 12 is also incorporated inside the loading unit 10.

The control unit 17 serves to control the operation of the measurement system MS1. The control unit 17 is provided with a microcomputer (referred to hereinbelow as CPU) 17b and a memory 17a. The CPU 17b is connected by a control line to the barcode reader 2, display lamps 11, display 14, printer 13, speaker 15, area sensor 16, and sensor 12. The CPU 17b controls the operation of the measurement system MS1 by executing a program stored in a memory 17a. Further, the CPU 17b calculates the measurement results on the basis of data acquired by the area sensor 16. If necessary, an interface circuit can be disposed between these constituent elements and the CPU 17b. The memory 17a is provided with a ROM region and a RAM region. The ROM region stores the operation program or parameters of the measurement system MS1. The RAM region temporarily stores the operation program and also patient's information read by the barcode reader 2 and data acquired by the area sensor 16.

The sensor 12 is disposed in the back of each loading unit 10 and serves to detect that the immunochromatographic test piece 4 has been loaded into the loading unit 10. The sensor 12 corresponds to an example of the detection means in accordance with the present invention. For example, a mechanical sensor can be used as the sensor 12. In addition to the mechanical sensor, an optical sensor provided with a light-emitting module and a light-receiving sensor module can be also used as the sensor 12. The area sensor 16 used for optical measurements can be also configured to serve also as such optical sensor.

The area sensor 16 is provided to be capable of moving in the direction of arrow N1 above the loading unit 10. The area sensor 16 corresponds to an example of the measurement means in accordance with the present invention. When the immunochromatographic test piece 4 has been loaded into the correct loading unit 10 according to the guidance from the display lamp 11, the area sensor 16 moves above this loading unit 10. The area sensor 16 initially reads the barcode 43 where the measurement items of the immunochromatographic test piece 4 have been recorded. Then, the area sensor 16 reads changes of color of the line 42c, which have appeared in the measurement window 42, as image data. The area sensor 16 is suitable for detecting stripe-like coloration such as that of the line 42c occurring on the surface of the support body 42a, as in the case of the immunochromatographic test piece 4.

[Measurement Method Using the Measurement System]

Figure 7:
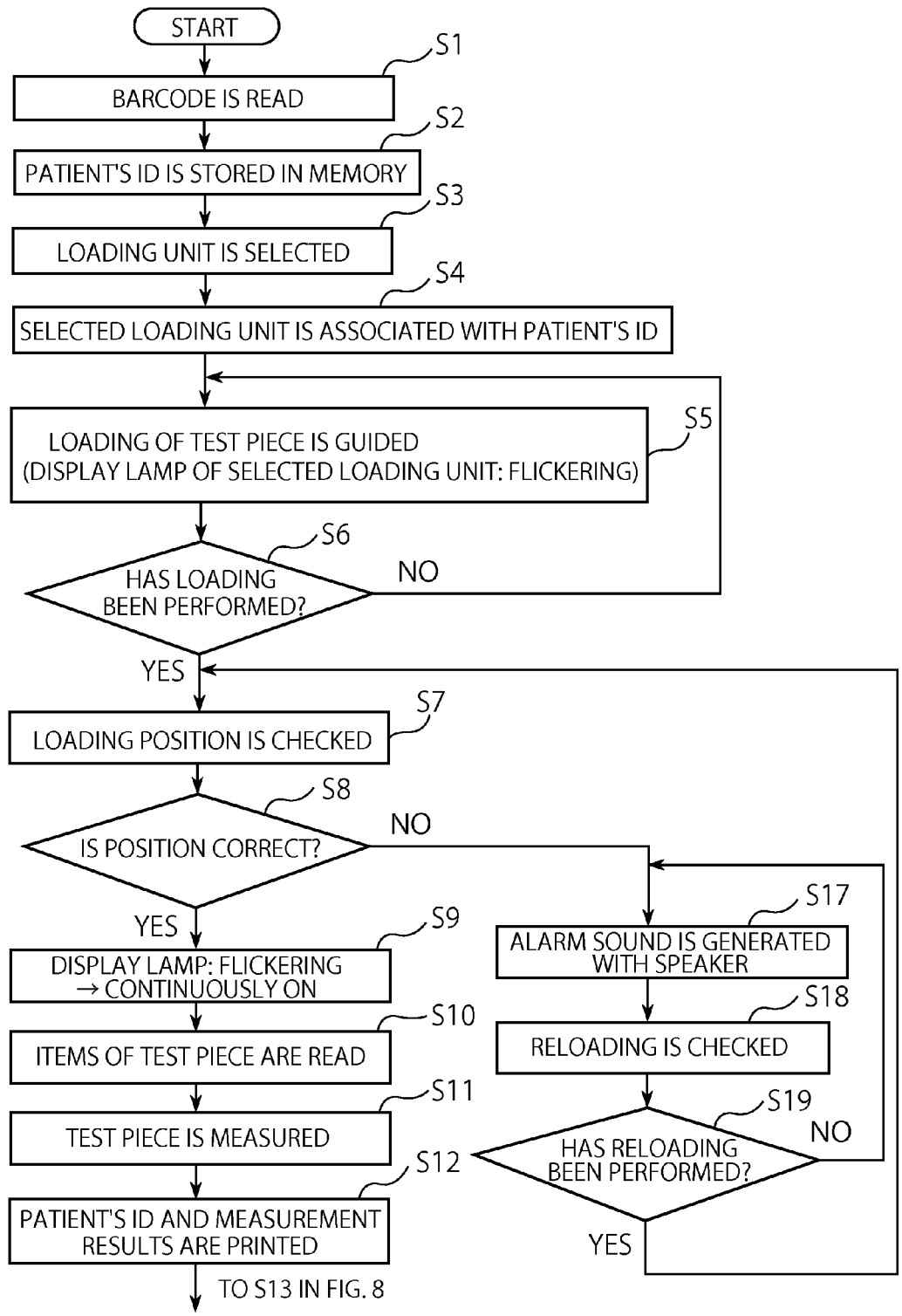
FIG. 7 is a flowchart illustrating part of an example of an operation processing sequence in the measurement system shown in FIG. 1.
Figure 8:
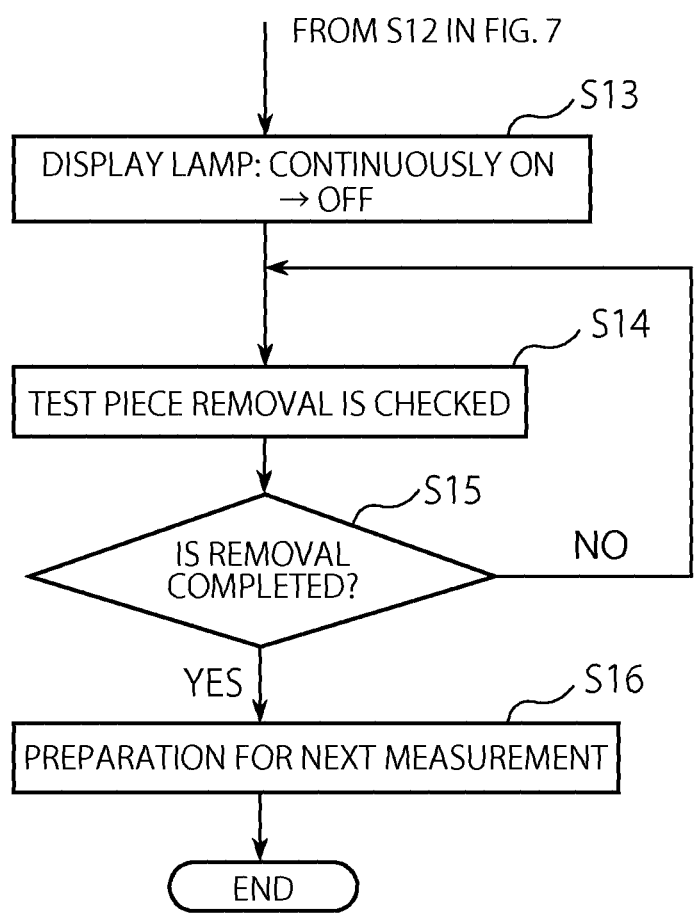
FIG. 8 is a flowchart illustrating part of an example of an operation processing sequence in the measurement system shown in FIG. 1.

An example of the measurement method performed by using the measurement system MS1 and an example of operation procedure executed by the control unit 17 to implement this measurement method will be explained below with reference to FIGS. 3 to 6 and also flowcharts shown in FIGS. 7 and 8.

Figure 3:
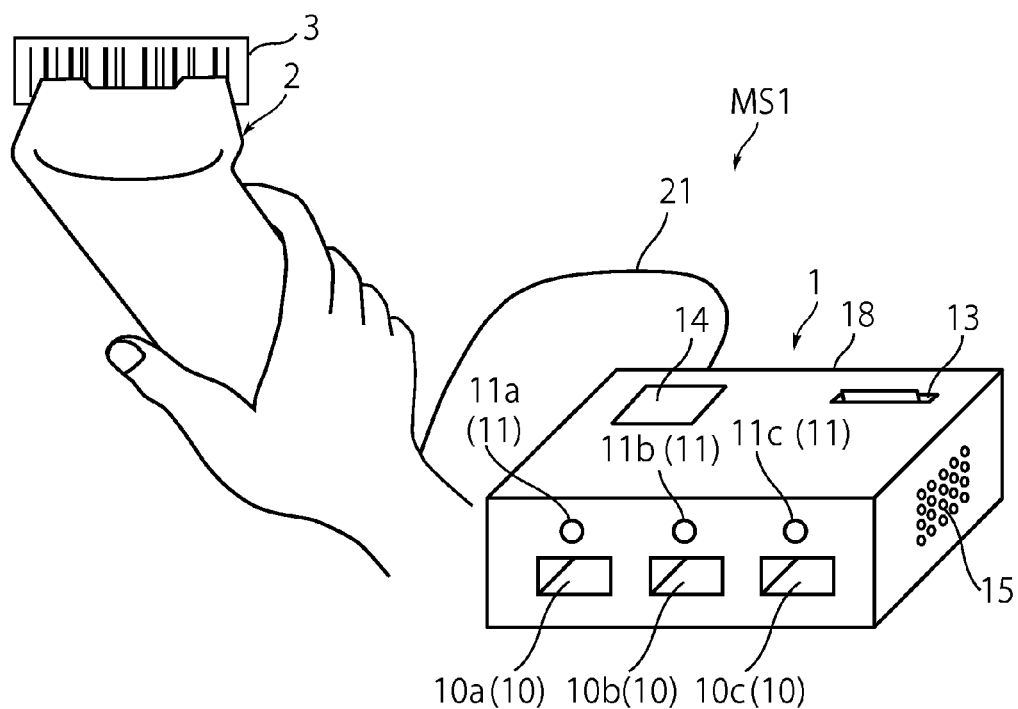
FIG. 3 is a perspective diagram illustrating the state in which the measurement system shown in FIG. 1 reads information on the analyte provider.

FIG. 3 illustrates a state in which the measurement system MS1 reads the patient's information. The barcode 3 which is attached to the patient's chart and in which patient's information including identification information has been recorded is read by the barcode reader 2 (S1). The patient's information including identification information that has been read is saved in the memory 17a located inside the measurement device 1 (S2). The control unit 17 selects, for example, the loading unit 10a from among the empty loading units 10 according to the preset rule (S3). When loading units 10 are selected, a plurality of loading units 10 may be selected so as to enable random selection by the user. The control unit 17 stores the patient's information including the identification information, which has been saved in the memory 17a, in association with the selected loading unit 10 in the memory 17a (S4). The patient who is an analyte provider is thus associated with the loading unit 10a. As mentioned hereinabove, the patient's identification information is, for example, patients ID number or patient's name.

Figure 4:
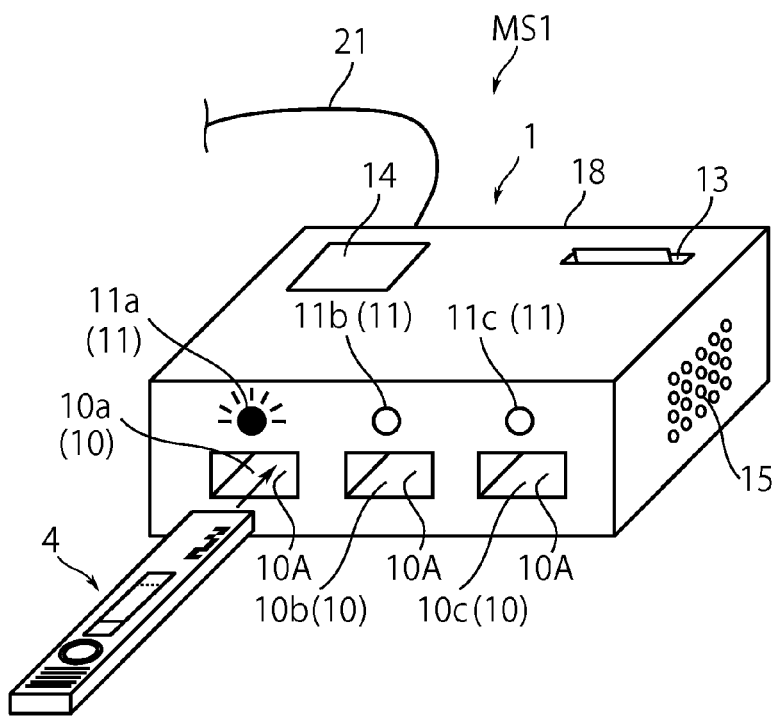
FIG. 4 is a perspective diagram illustrating the state in which the measurement system shown in FIG. 1 guides loading of a test piece.

FIG. 4 illustrates a state in which the measurement system MS1 guides the loading of the immunochromatographic test piece 4. After the processing of associating the patient's information including the identification information with the loading unit 10a performed by the control unit 17 has been completed, the display lamp 11a guides the immunochromatographic test piece 4 to which the patient's analyte has been applied, to the loading unit 10a as shown in FIG. 4 (S5). The guidance is performed by flickering of the display lamp 11a provided correspondingly to the selected loading unit 10a. When the immunochromatographic test piece 4 is not loaded, the guidance processing is continuously performed (S6: NO, S5).

When the immunochromatographic test piece 4 has been loaded through the opening 10A into a certain loading unit 10, it is determined whether or not the immunochromatographic test piece 4 has been correctly loaded to the location indicated by the display lamp 11a (S7). This determination is performed using the sensor 12 disposed in the back of the loading unit 10. When the sensors 12b, 12c of the loading units 10b, 10c different from the location indicated by the display lamp 11a output signals demonstrating that the immunochromatographic test piece 4 has been loaded, an alarm sound is generated by the speaker 15, thereby notifying the user of the error (S8: NO, S17), and a reloading check is performed (S18). Generating the alarm sound with the speaker 15 is not the only method suitable for notifying of the error. Thus, the error can be displayed, for example, by "NG" on the display 14 or in the output of the printer 13, or by changing the color or turning off the display lamp 11a. When no reloading is performed, the alarm sound is continuously generated by the speaker 15 (S19: NO, S17). When the reloading has been performed, the loading position is checked again (S19: YES, S7).

When a signal indicating that the immunochromatographic test piece 4 has been loaded is outputted by the sensor 12a of the display unit 10a indicated for loading by the display lamp 11a, the control unit 17 determines that the immunochromatographic test piece 4 has been loaded correctly and the display lamp 11a changes to a continuous ON mode (S8: YES, S9).

Figure 5:
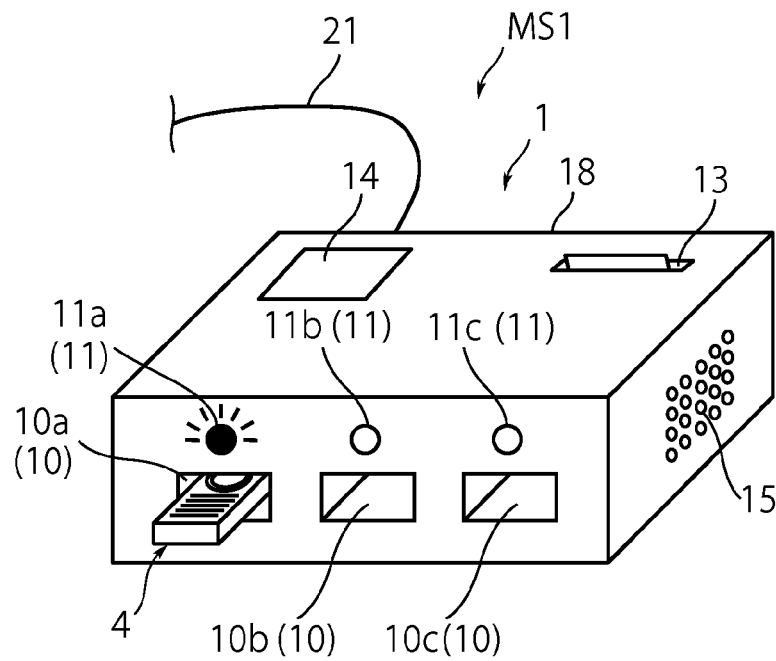
FIG. 5 is a perspective diagram illustrating the state in which the measurement system shown in FIG. 1 measures a test piece.

FIG. 5 illustrates a state in which the measurement system MS1 performs the measurements of the immunochromatographic test piece 4. Inside the measurement device 1, the area sensor 16 moves above the loading unit 10a and reads the identification barcode 43 provided on the case 40 of the immunochromatographic test piece 4 (S10). Then, the measurements of the immunochromatographic test piece 4 are performed (S11). The measurements are performed by acquiring image data of the line 42c on the support body 42a with the area sensor 16 after a reaction completion time established for each measurement item elapses since the immunochromatographic test piece 4 has been loaded into the loading unit 10a. The acquired data are sent to the control unit 17. The control unit 17 calculates the influenza virus amount, which is the measurement object, as a measurement result on the basis of the calibration curve stored in the memory 17a.

Figure 6:
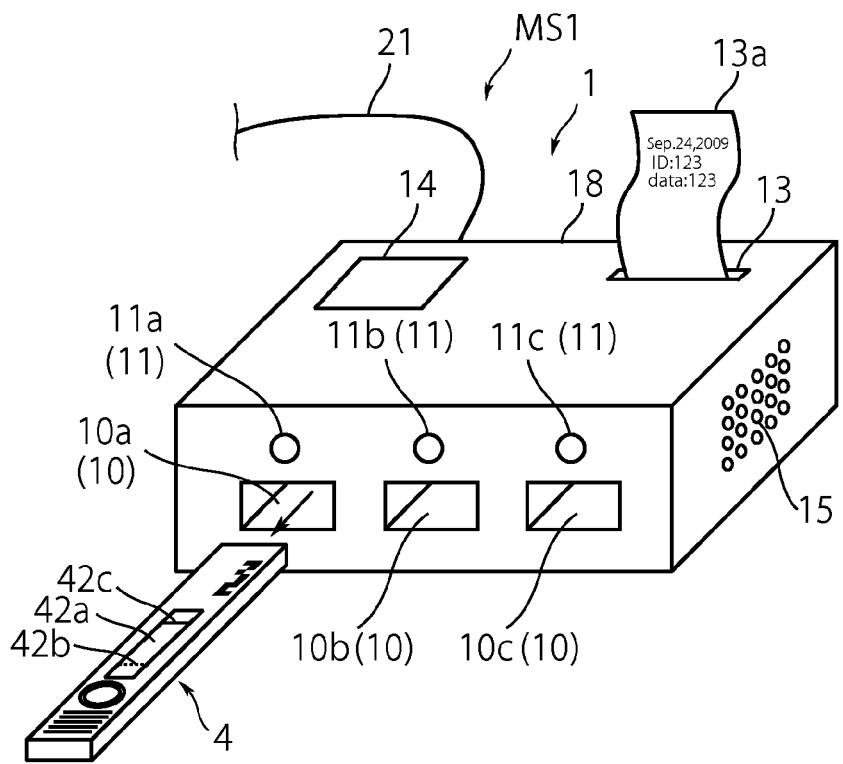
FIG. 6 is a perspective diagram illustrating the state in which the measurement system shown in FIG. 1 displays measurement results.

FIG. 6 illustrates a state in which the measurement system MS1 displays the measurement results. As shown in FIG. 6, when the measurements are completed, the printer 13 prints out the measurement date and time, patient's information including identification information, and measurement results on a printing paper 13a (S12). Then, the measurement results are sent to a host computer such as a personal computer (not shown in the figure). The control unit 17 then changes the operation state of the display lamp 11*a* from continuous ON to OFF (S13). It is then checked whether or not the immunochromatographic test piece 4 has been removed from the loading unit 10*a* (S14). When the removal has not been completed, the removal check is continuously performed (S15: NO, S14). Where the removal has been completed, preparation for the next measurement is performed (S16). Since the measurement system MS1 is provided with a plurality of loading units 10 that enable independent measurements, even if the measurement process has not yet been completed in one loading unit 10 (for example, loading unit 10*a*), the measurements can be started in another loading unit 10 (for example, loading unit 10*b* or 10*c*), and measurement results can be obtained individually.

As mentioned hereinabove, in the measurement system MS1, the immunochromatographic test piece 4 to which the analyte derived from a patient (analyte provider) has been applied is guided by switching on a display lamp (in the present embodiment, the display lamp 11*a*) to a special loading unit 10*a* that is individually associated with the patient on the basis of identification information on the patient that has been read by the barcode reader 2. As a result, the user of the present measurement system MS1 can load the immunochromatographic test piece 4 to the corresponding special loading unit 10*a* according to the guidance from the display lamp 11*a*, without memorizing the patient's ID and loading location. Therefore, the user can easily associate the patient's information including identification information that has been specified by reading with the barcode reader 2 with the measurement results obtained from the analyte derived from the patient. Further, the reliability of such association can be increased.

In the measurement system MS1, the above-described flow can be executed simultaneously and randomly in each of the loading units 10*a*, 10*b*, 10*c*. Even when a plurality of analytes derived from patients are simultaneously and randomly measured in the measurement system MS1, the user can easily associate the patient's information including identification information that has been specified by reading with the barcode reader 2 with the measurement results obtained from the analytes derived from the patients. Further, the reliability of such association can be increased.

[Other Embodiments]

FIGS. 9 to 12 illustrate another embodiment of the present invention. In these figures, elements similar or identical to those of the aforementioned embodiment are assigned with reference numerals same as in the aforementioned embodiment.

Figure 9:
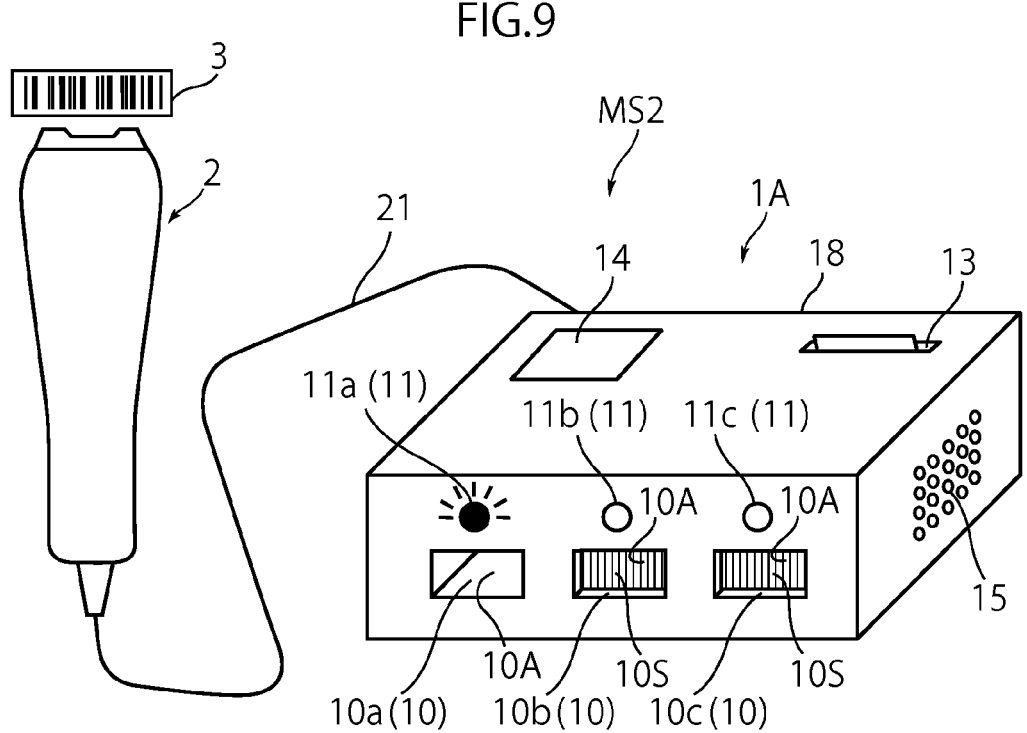
FIG. 9 is a perspective view illustrating another example of the entire measurement system in accordance with the present invention.

In the embodiment illustrated by FIG. 9, a measurement device 1A included in the measurement system MS2 has three loading units 10, similarly to the measurement system of the above-described embodiment, and also includes shutters 10S in addition to the display lamps 11. The display lamp 11 guides to the special loading unit selected by the lamp that is turned on, in the same manner as in the above-described embodiment. The shutters 10S are provided to prevent the immunochromatographic test piece 4 to which the specified analyte derived from the patient has been applied from being loaded to loading units 10*b*, 10*c* other than the selected special loading unit 10*a*. In other words, where the user reads patient's information including identification information recorded on the barcode 3 with the barcode reader 2, the shutters 10S are lowered so as to close the openings 10A of the loading units 10*b*, 10*c* which are not the special loading unit 10*a* selected so as to correspond to the identification information that has been read out. As a result, the immunochromatographic test piece 4 to which the specified analyte derived from the patient has been applied is guided to the special loading unit 10*a*. Thus, the user can easily associate the patient's information that has been specified by reading with the barcode reader 2 with the measurement results obtained from the analyte derived from the patient. Further, reliability of such association can be increased.

Figure 10:
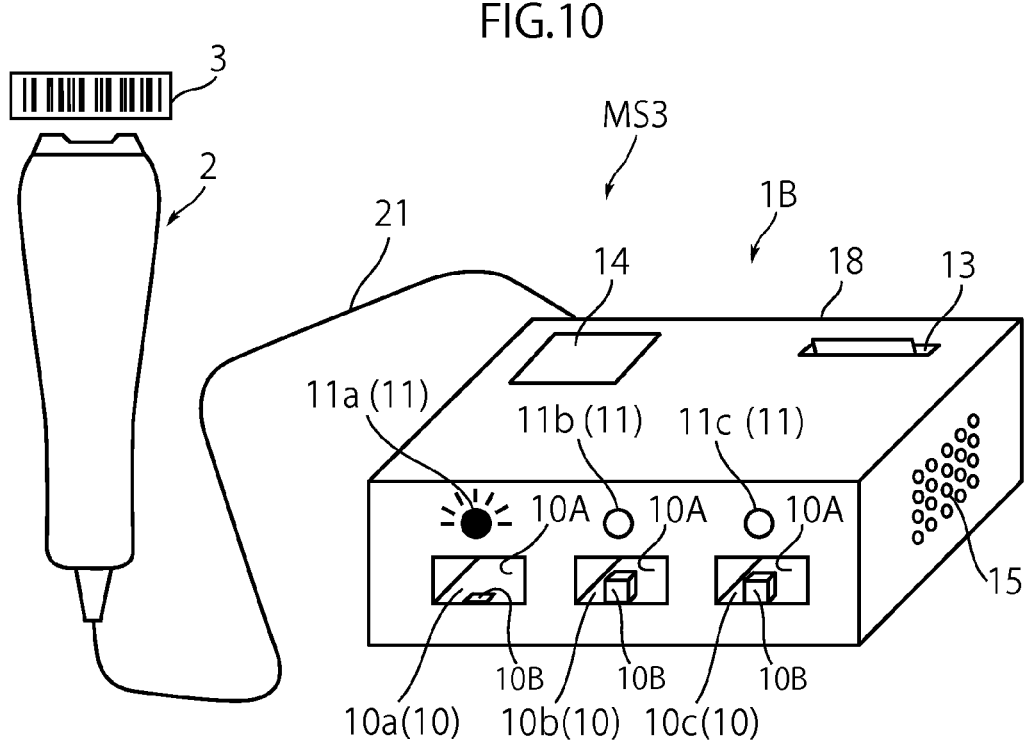
FIG. 10 is a perspective view illustrating another example of the entire measurement system in accordance with the present invention.

In the embodiment illustrated by FIG. 10, a measurement device 1B included in a measurement system MS3 is provided with blocks 10B instead of the shutters 10S of the embodiment illustrated by FIG. 9. The blocks 10B are configured to protrude in order to block the openings 10A of the loading units 10*b*, 10*c*, which are not the loading unit 10*a*, with the object of preventing the immunochromatographic test piece 4 from being loaded into the loading units 10*b*, 10*c* which are different from the selected special loading unit 10*a*. As a result, the user can easily associate the patient's information that has been specified by reading with the barcode reader 2 with the measurement results obtained from the analyte derived from the patient. Further, the reliability of such association can be increased. The above-described shutters 10S and blocks 10B correspond to an example of the preventing means in accordance with the present invention. The structure including shutters 10S and the structure including blocks 10B can be used together as the prevention means.

Figure 11:
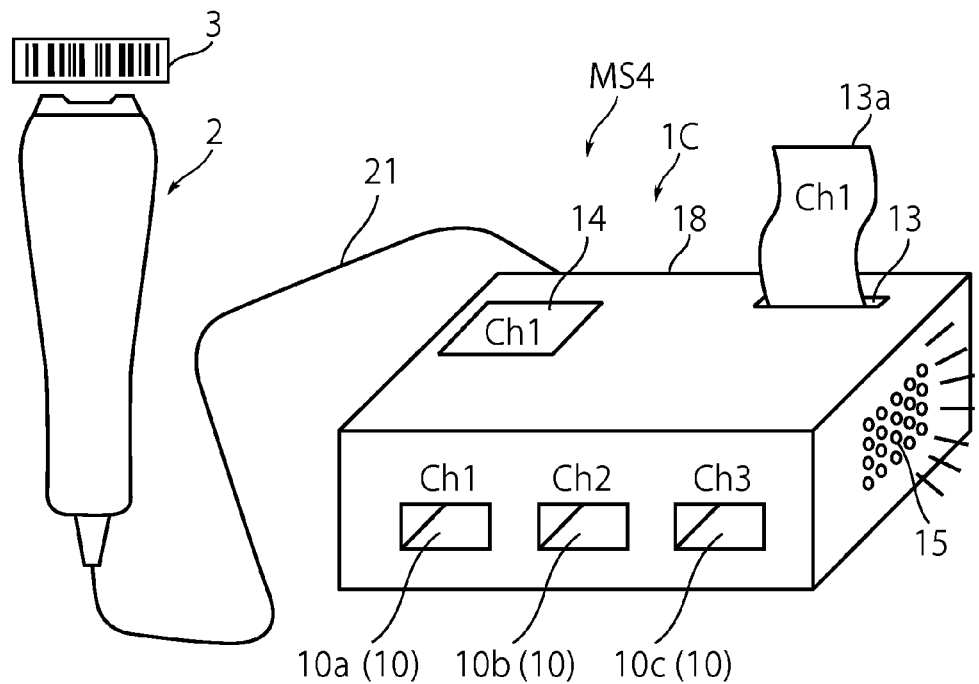
FIG. 11 is a perspective view illustrating another example of the entire measurement system in accordance with the present invention.

In the embodiment illustrated by FIG. 11, three loading units 10*a*, 10*b*, 10*c* and channel numbers (in FIG. 11, CH1, CH2, CH3) corresponding to the loading units 10*a*, 10*b*, 10*c*, respectively, are provided in a measurement device 1C included in a measurement system MS4. For example, when control unit of the measurement device 1C has selected the loading unit 10*a* as the loading unit 10 that should be associated with the patient's information including identification information that has been read by the barcode reader 2, a display unit 14 of the measurement device 1C displays the channel number "CH1". As a result, the measurement device 1C can show to the user which loading unit 10 is the selected special loading unit. Thus, the user can easily associate the patient's information that has been specified by reading with the barcode reader 2 with the measurement results obtained from the analyte derived from the patient. Further, the reliability of such association can be increased. The display unit 14 has a function of the guidance means for guiding the loading of a measurement tool such as the immunochromatographic test piece 4 and also can function as a display that shows measurement results.

Further, in the measurement system MS4 depicted in FIG. 11, for example, the printer 13 incorporating a thermal printing head can be used as the guidance means. For example, when the control unit of the measurement device 1C has selected the loading unit 10*a* as the loading unit 10 that is to be associated with the patient's information including the identification information that has been read by the barcode reader 2, the printer 13 of the measurement device 1C prints the channel number (in this case, CH1), thereby displaying that the loading unit 10*a* has been selected. Thus, the user can easily associate the patient's information including the specified identification information with the measurement results obtained from the analyte derived from the patient. Further, the reliability of such association can be increased. The printer 13 also can include the function of a usual printer that prints and outputs as a paper document the results obtained in measuring the changes caused by a reaction proceeding inside or on the surface of the immunochromatographic test piece 4.

Furthermore, in the measurement system MS4 depicted in FIG. 11, a speaker 15 can be used as the guidance means. The speaker 15 of the measurement device 1C can issue an audio message such as "PLEASE, LOAD IN CH1" in order to indicate the selected special loading unit (in this case, CH1) to the user. The speaker 15 not only can pronounce the channel number as mentioned hereinabove, but also can guide the user by pronouncing relative position information, for example, by the message "THE LOADING UNIT IS ON THE RIGHT END". In addition to the information indicating the position of the loading unit, the speaker 15 can also issue an audio message providing measurement result information such as "THE MEASUREMENT RESULT IS 120 mg/dl". Thus, the user can easily associate the patient's information that has been specified by reading with the barcode reader 2 with the measurement results obtained from the analyte derived from the patient. Further, the reliability of such association can be increased. The speaker 15 can also serve as a speaker for issuing various warning sounds (buzzer sounds) for the entire measurement system MS4.

The description of the channel number on the measurement device 1C can be performed by coating, pad printing, gravure printing, and by using a mold with depressions and protrusions when the measurement device body is molded, and the method therefor is not particularly limited.

Figure 12:
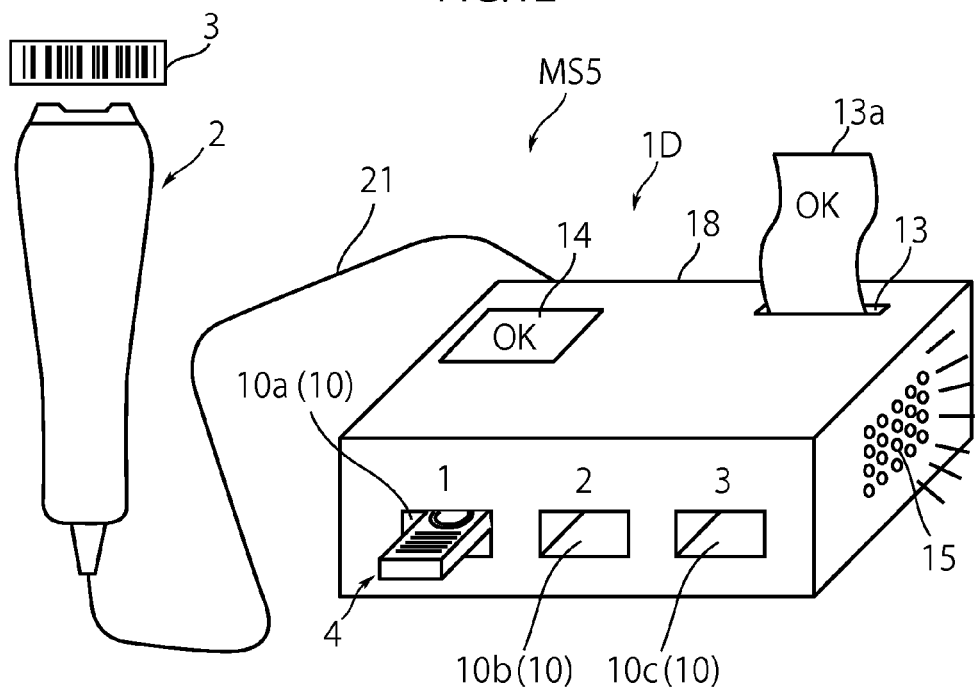
FIG. 12 is a perspective view illustrating another example of the entire measurement system in accordance with the present invention.

In the embodiment illustrated by FIG. 12, a measurement system MS5 uses a method of notifying the user of the correct loading of the measurement tool such as the immunochromatographic test piece 4 to the indicated location. Thus, the OK message or the like is displayed on a display device such as the display 14 or printer 13 provided in a measurement device 1D. This notification can be also performed with the speaker 15. The user can thus be easily and reliably notified of loading of the measurement tool such as the immunochromatographic test piece 4 to the correct loading unit 10 selected by the control unit of the measurement device 1D.

Figure 13:
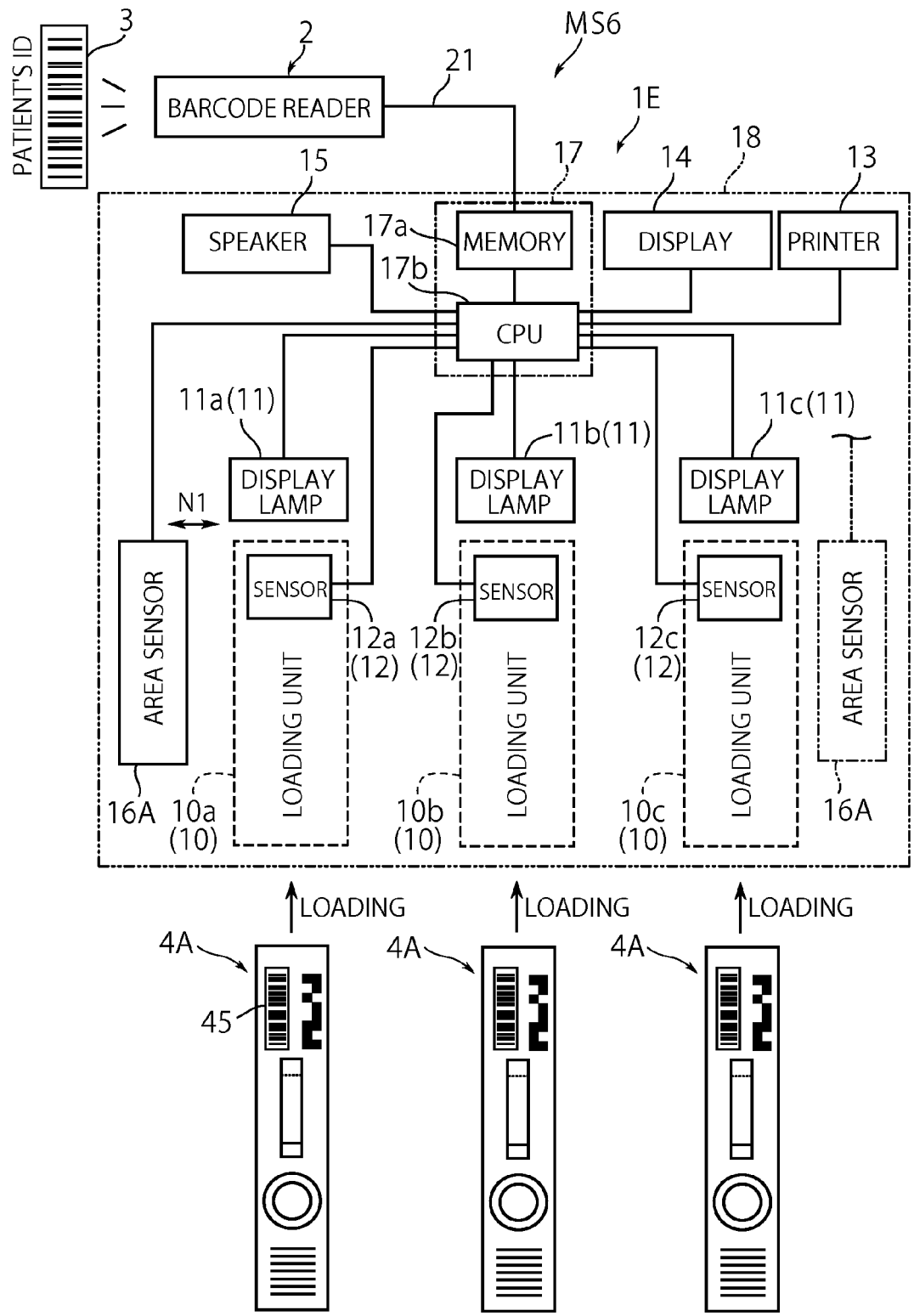
FIG. 13 is a block diagram illustrating another example of the measurement system in accordance with the present invention.

In the embodiment illustrated by FIG. 13, a control unit 17 included in a measurement system MS6 is configured to compare the patient's information including identification information that has been recorder on the barcode 3 attached to the chart or analyte container and read by the barcode reader 2 or the like with the information recorded on a barcode 45 attached to an immunochromatographic test piece 4A. For example, a number that has been assigned in advance to the immunochromatographic test piece 4A is coded and recorded on the case of the immunochromatographic test piece 4A, and this number is also recorded as part of the patient's information (barcode 3) that has been attached to the chart or the like and is the first to be read. The immunochromatographic test piece 4A is guided by the display lamp 11 and loaded to the loading unit 10 of a measurement device 1E. The control unit 17 determines whether the number information that has been read by an area sensor 16A disposed inside the loading unit 10 is identical to the number information assigned to the immunochromatographic test piece 4A and contained in the patient's information that has been initially read. Where the numbers do not match each other, the speaker 15 issues a warning sound, thereby notifying the user of the error in the loading position. The frequency of mishandling the analyte can thus be decreased and therefore the reliability of associating the patient's information that has been read in advance by the barcode reader 2 with the measurement results obtained from the analyte derived from the patient can be further increased. The barcode 45 attached to the immunochromatographic test piece 4A may be the record of individual information on the patient. In this case, it is determined whether or not the information matches by comparing the patient's identification information that has been read by the barcode reader 2 with the patient's identification information recorded on the barcode 45 attached to the immunochromatographic test piece 4A.

The present invention is not limited to the contents of the above-described embodiments.

Specific types of the analyte to be analyzed by the measurement system in accordance with the present invention are not particularly limited. The analyte is not limited to a liquid sample from a mucous membrane of the patient's pharynx or nasal cavity and can be a body fluid such as urine, blood, and saliva, or other substances.

The measurement tool used in the measurement system in accordance with the present invention is not limited to the immunochromatographic test piece 4, and a test piece in which a reagent layer impregnated with a chemical reaction agent is attached to a support body or a measurement tool in which a dry reagent or a liquid reagent is sealed in a disposable measurement cell can be also used. Biosensor-type test pieces for performing electrochemical measurements can be also used as the measurement tools. A biosensor-type test piece is typically provided with a conductive electrode and an oxidation-reduction enzyme that induces an electron exchange reaction with the desired component in an analyte on a support body. In this case, the measurement device includes as measurement means a conductive connector that comes into contact with the conductive electrode in the back of a loading unit. The oxidation-reduction enzyme reacts with the desired component on the support body, an electric current generated proportionally to the concentration of the desired component is measured, and the amount of the desired component is calculated.

The reading means used in the measurement system in accordance with the present invention is disclosed in the above-described embodiments by way of example as a combination of the barcode 3 and the barcode reader 2, but such configuration is not limiting. It is also possible to use a touch panel as a display of the measurement device, call out and display on the touch panel the information on patients that has been acquired in advance, includes a plurality of identification data, and relates to patients scheduled for the measurements. The user then can select the information on a specific patient by touching the information relating to the patient that should be specified (display such as an ID number or name).

The measurement means used in the measurement system in accordance with the present invention is not limited to the area sensor 16. An optical sensor unit constituted by a combination of a light-emitting module incorporating a LED that emits light of a predetermined wavelength and a light-receiving sensor module in which a plurality of photodiodes are arranged is an example of another suitable optical measurement means. Such optical sensor unit is suitable for detecting coloration occurring in the entire surface area of the test piece to which the analyte is applied.

In the measurement system in accordance with the present invention, the measurements can be also performed by loading the measurement tool into the empty loading unit 10, without reading the patient's information. The measurements in which the patient's information is not associated with the measurement results obtained from the analyte derived from the patient can be performed in parallel with the measurements involving such association.

The invention claimed is:
1. A measurement system, comprising:
 a measurement device configured to perform measurements of a measurement tool to which an analyte derived from an analyte provider has been or is to be applied, the measuring tool supporting a measurement reagent; and a reading unit configured to read information on the analyte provider that includes identification information, wherein the measurement device comprises: a main body case, the main body case comprising:
a plurality of loading units configured to load the measurement tool, where each of the plurality of loading units includes a sensor capable of recognizing that the measurement tool has been loaded;
a control unit configured to execute an operation control for the measurement device, where the control unit is connected to the reading unit and the plurality of loading units, and where the control unit is further configured to receive the analyte provider information read by the reading unit, and to select a loading unit from among the plurality of loading units as a special loading unit for the analyte derived from the analyte provider, where the special loading unit is individually associated in advance with the analyte provider based on the identification information;
a guidance unit connected to the control unit, where the guidance unit is disposed on the main body case to correspond to each of the plurality of loading units, where the guidance unit is configured to guide a user to load the special loading unit with the measurement tool according to the operation control b the control unit; and
a measurement unit provided inside the main body case separately from the reading unit and connected to the control unit, the measurement unit arranged to perform measurements of the measurement tool loaded into each of the plurality of loading units, the measurement unit configured to start measurements of the measurement tool upon detection that the measurement tool has been loaded into the special loading unit.

2. The measurement system according to claim 1, wherein the guidance units comprise a plurality of display lamps disposed to correspond to the plurality of loading units, where the display lamps are configured to perform guidance by being turned on, turned off, or by changing color.

3. The measurement system according to claim 1, wherein the guidance unit is a prevention unit configured to prevent the measurement tool from being loaded into a loading unit other than the special loading unit that has been individually associated with the analyte provider.

4. The measurement system according to claim 3, wherein each of the plurality of loading units is provided with an opening for loading the measurement tool, where the prevention unit is configured to close the opening of the other loading unit.

5. The measurement system according to claim 1, wherein the guidance unit is a display device configured to display position information of the special loading unit that has been individually associated with the analyte provider.

6. The measurement system according to claim 1, wherein the analyte provider information is recorded as a barcode, and the reading unit is at least one of a barcode reader and an image recognition camera.

7. The measurement system according to claim 1, wherein the reading unit comprises a touch panel, where the analyte provider information is listed and displayed in advance on the touch panel, and a user is capable of selecting by touch, specific information from the information that has been listed and displayed on the touch panel.

8. The measurement system according to claim 1, wherein the sensor is disposed in the back of each of the plurality of loading units.

9. The measurement system according to claim 1, further comprising a warning unit configured to warn when the measurement tool has been erroneously loaded, when the sensor detects that the measurement tool having applied thereto the analyte derived from the analyte provider specified by the information read by the reading unit, has been loaded to a loading unit other than the special loading unit individually associated with the analyte provider.

* * * * *